(12) United States Patent
Marchesi

(10) Patent No.: US 6,409,744 B1
(45) Date of Patent: Jun. 25, 2002

(54) HUMAN-BODY IRRADIATION DEVICE FOR DEEP TREATMENT OF TISSUES

(76) Inventor: Fabio Paolo Marchesi, Via Tadino, 13, 20124 Milan (IT)

( * ) Notice: Subject to any disclaimer, the term of this patent is extended or adjusted under 35 U.S.C. 154(b) by 0 days.

(21) Appl. No.: 09/507,160

(22) Filed: Feb. 18, 2000

(30) Foreign Application Priority Data

Feb. 19, 1999 (IT) .......................................... MI99A0339

(51) Int. Cl.⁷ .................................................. A61F 7/00
(52) U.S. Cl. ............................. 607/96; 607/88; 607/90; 607/100; 606/9; 606/13
(58) Field of Search ............................... 607/77, 88–94, 607/96, 100, 108; 606/9, 10, 13, 27; 128/898

(56) References Cited

U.S. PATENT DOCUMENTS 3,648,706 A * 3/1972 Holzer ........................ 128/395
5,660,836 A * 8/1997 Knowlton ..................... 424/400
5,849,026 A * 12/1998 Zhou et al. ..................... 607/90
6,024,760 A * 2/2000 Marchesi ....................... 607/96

FOREIGN PATENT DOCUMENTS

EP        0764039 B1  * 10/1999  ............ A61N/5/06

* cited by examiner

Primary Examiner—John Mulcahy
Assistant Examiner—A. Farah
(74) Attorney, Agent, or Firm—Shlesinger, Fitzsimmons & Shlesinger

(57) ABSTRACT

A device for emission of red/infrared light radiation for treatment of a human body comprises red/infrared lamps (11) and lamp-emission modulating means (12) which modulates the emission between a low level and a high level with a modulation period included between 0.1 and 20 seconds.

16 Claims, 2 Drawing Sheets

HUMAN-BODY IRRADIATION DEVICE FOR DEEP TREATMENT OF TISSUES

BACKGROUND OF THE INVENTION

The present invention relates to a human-body irradiation device with light radiation in the red/infrared region. Applications are known in which the human body is submitted to a continuous infrared or ultraviolet irradiation to carry out localised slimming treatments, for example. In the European Patent No. 0 764 039 continuous irradiation combined with a simultaneous physical activity is described.

In the known art a relationship between an increase in the radiated power and the treatment efficiency has been noticed. Higher powers would enable a greater deep heating to be achieved, making heat reach those points where it is more necessary for radiation efficiency. Unfortunately, the radiated power cannot be increased beyond relatively low levels without giving rise to skin reddening or, even worse, to skin burns.

In U.S. Pat. No. 3,648,706 it is described a human-body irradiation device in which rows of incandescent, ultraviolet or infrared light lamps are caused to be sequentially and individually switched on to generate radiating waves intended for sliding along the surface of a patient's body so as to avoid heat concentrations over the whole irradiated surface. In order to achieve this result, many rows of lamps are provided, each of which is turned off during the switching-on phases of the other rows. U.S. Pat. No. 3,648,706 aims at having a given energy distribution over the skin surface; on the contrary, it does not deal with deep heating of tissues. This solution does not therefore enable an optimal and uniform heating of the upper and lower layers of the subcutaneous tissues to be obtained.

It is a general aim of the present invention to provide an increase in the efficiency of the irradiating action, without the mentioned side effects.

SUMMARY OF THE INVENTION

In view of this aim, in accordance with the invention, a device for emission of red/infrared light radiation for treatment of the human body has been devised, which comprises red/infrared lamps and lamp-emission modulating means which modulates the light emission between a low level and a high level with a modulation period included between 0.1 and 20 seconds, the high-level duration being included between ⅔ and 8/10 of the modulation period.

BRIEF DESCRIPTION OF THE DRAWINGS

For better explaining the innovative principles of the present invention and the advantages it offers over the known art, a possible embodiment applying these principles will be described hereinafter, by way of non-limiting example, with the aid of the accompanying drawings. In the drawings.

DETAILED DESCRIPTION OF THE INVENTION

Figure 1:
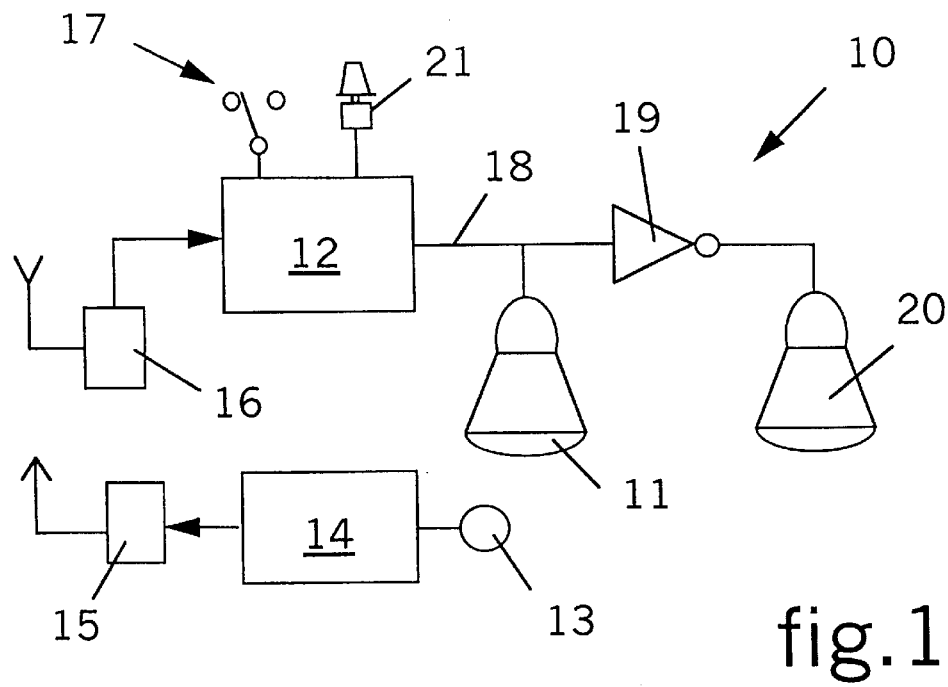
FIG. 1 is a diagrammatic view of a red/infrared emission device made in accordance with the invention.

With reference to the drawings, shown in FIG. 1 is a block diagram of a device, generally identified by 10, for emission of red/infrared light radiation for treatment of the human body. The device comprises lamps 11 with emission at frequencies included between the red and infrared regions and means 12 for modulating the emission of these lamps. The modulating means 12 modulates the red/infrared emission between a low level and a high level, with a modulation period T included between 0.1 and 20 seconds and a duration of the high level included between ⅔ and 8/10 of the modulation period T.

Advantageously, the high level corresponds to a rated emission value of the lamps, whereas the low level corresponds to a substantially zero emission.

A preferred way for controlling emission modulation is that of accomplishing the modulating means 12 in a manner adapted to control supply 18 to the lamps with a modulation envelope which is a function of the desired modulation. For example, if the supply voltage is a sinusoidal voltage, this sinusoidal voltage will be modulated with an appropriate envelope for achieving the desired emission between the maximum value and minimum value with the desired period. The maximum value may correspond to a full lamp supply (or a full-supply percentage) and the minimum value to the absence of supply (or a full-supply percentage of a lower value than the maximum value).

It has been surprisingly found that the emission modulation according to the above mentioned parameters gives an important increase in the treatment efficiency as compared to the known art consisting in carrying out a continuous irradiation over the whole treatment duration. In particular, a greater efficiency obtained in deeply heating the tissues with a reduction in the side effects on surface tissues due to excessive heating is obtained. Infrared lamps available on the market generally are quartz-iodine or filament lamps and have a frequency response extending from the visible spectrum to about 4 microns.

The visible light has a wavelength from about 0.35 to 0.690 micron, in which frequencies corresponding to all colours are present. Infrared rays, on the contrary, have a wavelength from about 0.7 micron to about 5 microns. Of these relatively wide frequency range, frequencies having greater capability to penetrate into the human tissues of the epidermis and the subcutaneous fat are those included between 0.8 and 1.2 micron, whereas frequencies higher than 1.5 micron generally stop on the tissue surface. In order to avoid overheating of the epidermis due to frequencies that do not succeed in penetrating deeply, there are two possible solutions: either making optical band-pass filters adapted to enable passage of only those frequencies capable of penetrating deeply, by "mechanically" eliminating those frequencies that, stopping on the surface, could cause burns to the epidermis using powers usually required for efficiently heating the deep subcutaneous fat too, or adopting the solution being the object of the present invention, i.e. utilising flashing lamps.

A longer period of time is required for the deep fat being heated as compared with surface fat or epidermis, and at the same time a longer period of time is required for the deep fat to be cooled as compared with surface fat. Through exploitation of the different "inertia" to heating and "cooling", by switching on and off the infrared sources following stated times, it is possible to use higher powers (as compared with a constant lighting) without running the risk of overheating the epidermis and subcutaneous surface fat, while on the contrary efficiently heating the deep subcutaneous fat which, on the other hand, has not enough time to "cool" between a switching-off pause and the subsequent one.

Infrared rays, and in particular some specific frequencies of infrared rays, have the property of succeeding in efficiently heating the body fat deeply, even if this fat is an exceptional heat insulator.

The amount of infrared electromagnetic energy transferred to the tissue and converted to thermal energy by the latter, decreases as it penetrates more deeply, due to the increasingly more limited range of frequencies capable of reaching the deep layers. If, for instance, all frequencies included between 0.7 and 4 microns produced by an infrared source reach and heat the epidermis and surface fat, only frequencies included between 0.8 and 1.2 micron reach the fat located at some centimetres of depth and only after transferring part of their energy to the tissues they have passed through. For the above reason the increase in the tissue temperature is, at all events, unable to be uniform and is greater for surface layers. On cooling instead just the opposite occurs, as surface layers cool much quicker than deep layers. By exploiting this different inertia and introducing flashing of the infrared source, the temperature increase is made more uniform.

In short, the invention is based on the principle that heat can be transferred from one body to another by contact, by convection or by radiation. Since fat is an exceptional heat insulator, its thermal conductivity by contact is very limited and therefore the deep subcutaneous fat, once it has been heated by infrared rays, hardly succeeds in cooling during the switching-off pauses of the infrared source, taking into account the fact that it could do it only by contact. On the contrary, the subcutaneous surface fat can give heat back to the surrounding environment both by contact and by convection and radiation, without considering the fact that cooling is very quick on the surface if perspiration occurs, due to water evaporation.

Using a flashing infrared source therefore enables a greater uniformity in the increase of the tissue temperature to be achieved, which will bring about important advantages in terms both of general efficiency of the treatments and elimination of the dangerous side effects resulting from an excessive overheating of the epidermis.

In addition, a further advantage obtained by the discontinuous radiation embodied by the invention is that of avoiding the risk of reddening and of burns on the treated parts, which on the contrary occurs in the known art, when one is inclined to merely increase the radiated power in order to augment the deep thermal effect and, as a result, the efficiency of the application.

In other words, it has been found that the flashing action following the above mentioned parameters not only enables tissues to be exposed, without producing surface burns, to the action of a greater amount of electromagnetic energy in absolute value, than the tolerable energy in case of a continuous exposure, but the deep thermal effect, and consequently the radiation efficiency, greatly increases also with use of altogether smaller amounts of total radiated energy.

An explanation comes from the fact that since derma and epidermis (few millimetres in depth) are directly in contact with air, they cool more quickly than the deeper fat layers which are thermally very insulated. This different "inertia" to cooling allows the epidermis submitted to the flashing radiation action to have sufficiently long pauses for dispersing surface heat. Therefore, with flashing it is possible to distribute the electromagnetic energy of the infrared rays in a more efficient manner as far as the deeper layers of the subcutaneous fat, while avoiding the risk of surface burns. By way of example, it has been found possible to carry out a radiation with excellent results at a distance of 30 cm from the radiated surface, with a source of a wavelength included between 600 and 1600 nm, with a specific power (at a 780 nm wavelength) equal to 21 mwatt/cm$^2$ with Ta=¾T for 40 minutes (Ta=high-level time during period T). Should not modulation be carried out, the same power at all events would have been too great and could have caused surface burns with exposure times lower than 10 minutes, therefore with an undoubtedly lower amount of overall energy.

A particularly efficient emission has been found to be that with a wavelength included between 0.76 and 1.5 micron. These frequencies are those that have proved a greater capability of penetration into the deep tissues.

As a further improvement, it has been found useful to combine the infrared emission with a blue/ultraviolet emission. For the purpose blue/ultraviolet lamps 20 can be provided, which are connected with the modulating means 12 through an inverter 19 so as to modulate the ultraviolet emission in counter-phase with respect to the emission of infrared lamps. In other words, while the infrared emission is at a high level, the ultraviolet emission is at a low level and vice versa.

Carrying out the radiation modulation by putting it in connection (by synchronising it, for example) with the irradiated subject's heartbeat has been also found particularly efficient.

For the purpose, the device 10 may comprise means 14 for heartbeat detection, connected with the modulations means 12 for controlling modulation depending on the detected heartbeat. For detection, means 14 has sensors 13 that can be of any known type, such as conductive electrodes for detection of the electrophysiological potentials, reflection transducers or transmittance transducers for detection of blood flow variations, etc.

Advantageously, connection between the heartbeat detection means and modulating means is carried out through a cordless connection, so as to enable the treated subject to have more movement freedom. In particular, cordless connection can be a connection by radio or by infrared rays, obtained by means of an appropriate transmitter 15 and receiver 16.

Among possible synchronisations between modulation and heartbeat, particularly efficient were found those controlling passage between one level and the other on detection of a systole or diastole in the heartbeat. A command 17 is provided which enables one to manually key in at which of the two events modulation is to be synchronised.

Figure 2:
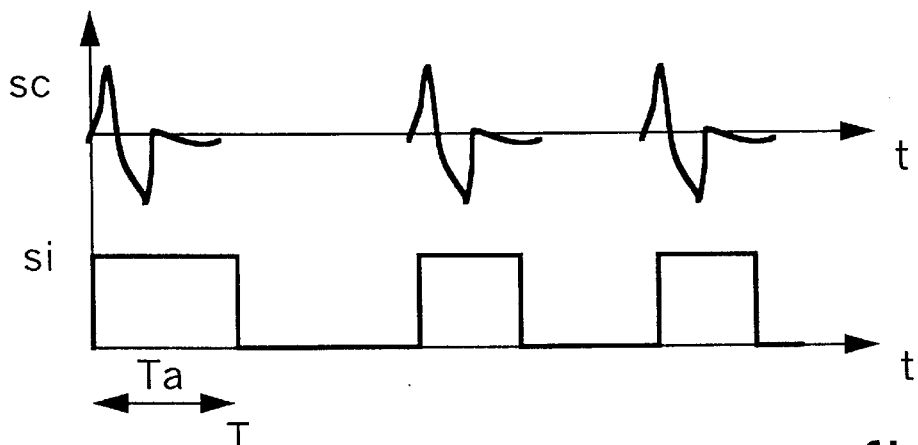
FIG. 2 is a graph of the possible link between heartbeat and emission in the device in FIG. 1.

Shown in FIG. 2 is a graph on which possible synchronisation between heartbeat (line $s_c$) and passage from a low radiation level to a high radiation level (line $s_i$) is represented. In the graph it is shown that, after the controlled passage, the achieved level is maintained over a predetermined period of time Ta, with Ta<T. It is advantageous for Ta to be lower than the time between two successive heartbeats.

At all events, it has been found advantageous for the high-level time Ta to be included between ⅔ T and ⁸⁄₁₀ T. This is also valid in the case of absence of synchronisation. Period Ta can be keyed in between a minimum value and a maximum value (expressed for example as percentages of T) by means of a command 21.

Figure 3:
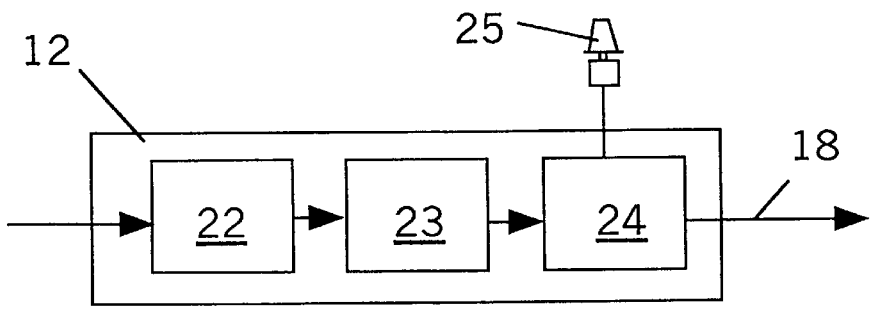
FIG. 3 is a view of an alternative embodiment of the device in FIG. 1.

Shown in FIG. 3 is a further improvement according to which modulation is controlled based on a heartbeat expectation, or the distance between two heartbeats, and not directly controlled by the heartbeat. This may be necessary when an advance in the transition between low and high levels is wished, both due to physiological reasons and in the case in which lamps have an inertia that would bring to a delay in the real transition in radiation relative to the desired instant.

For the purpose, means 21 is provided for measuring the average time between detected heartbeats, means 23 for calculating the expected instant for the next heartbeat starting from said average time, means 24 for controlling modulation with a predetermined advance relative to said expected instant for the next heartbeat. The control means 24 may comprise means 25 for keying in the desired advance. In addition to a forecasting device in real time, passage to a high level may also be provided to be delayed by a time interval almost equal to that between two heartbeats, so that one heartbeat controls passage, but this passage actually takes place with a predetermined slight advance relative to the next heartbeat.

Figure 4:
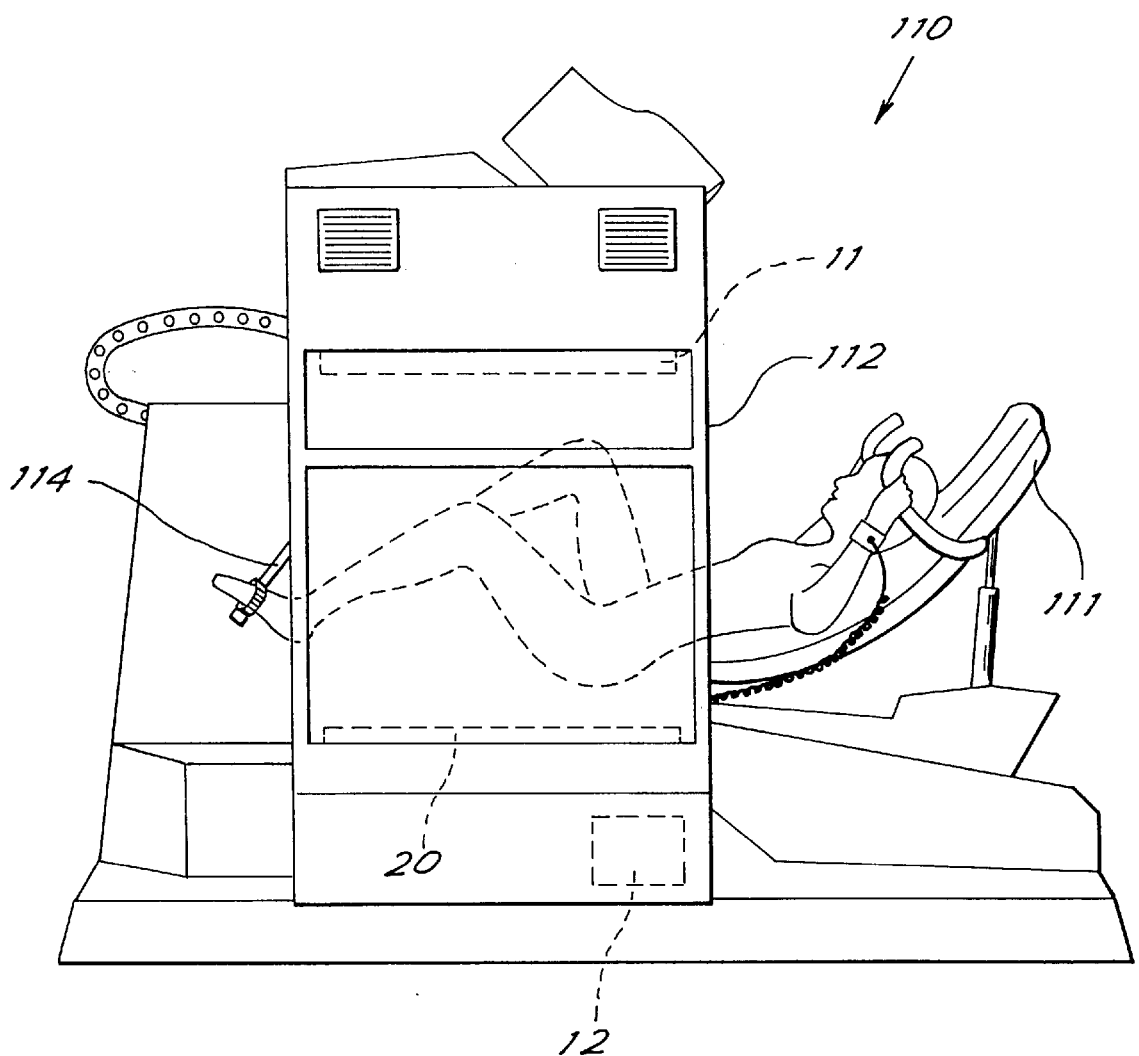
FIG. 4 is a possible application of the emission device in accordance with the invention.

Shown in FIG. 4 is a possible application of the principles of the invention to a machine, generally denoted by 110, with radiation and simultaneous physical activity. The machine comprises a seat 111 on which the user lies down so as to introduce his/her body into a booth 112, containing infrared lamps 11 and possibly ultraviolet lamps 20 and to simultaneously pedal on suitably braked pedals 114. A machine of this type is already generally described in the above mentioned European Patent No. 0 764 039. In accordance with the principles of the present invention, the machine is provided with means 13 (in the form of a detection armband, for example) for detection of the user's heartbeat. The control box 12 that can also be integrated into the operating unit of the machine, operates lamps 11 and 20 as already described above.

At this point it is apparent that the intended purposes are achieved.

Obviously, the above description of an embodiment applying the innovatory principles of the present invention is given by way of example only and therefore must not be considered as a limitation of the scope of the invention as herein claimed.

For instance, the circuit embodying the device may be comprised both of a wired logic and a suitably programmed microprocessor, as a person skilled in the art can easily conceive. In addition, as an alternative to a modulation of the emission obtained by variations in the lamps' supply voltage, a modulation directly acting on the emitted infrared light, through controlled filters for example such as electronically- or mechanically-controlled polarisation filters, may be employed.

Obviously, the ratio between the lamps' switching-on and switching-off time can be selected each time, depending on the features of the emitted radiating frequency. For instance, when radiations involving a high absorption by the surface skin layer are used, it is appropriate that a high ratio between the switching-on time and the switching-off time will be selected so as to promote heating of the deeper layers. Vice versa, in the case of radiations characterised by a high penetration into the deep layers, it is appropriate that a low ratio between the switching-on time and the switching-off time will be selected, in order not to overheat the lower layers.

What is claimed is:

1. A device for emission of red/infrared light radiation for treatment of the human body comprising red/infrared lamps and lamp-emission modulating means which modulates the red/infrared emission between a low level and a high level with a modulation period included between 0.1 and 20 seconds, the high-level duration being included between $2/3$ and $8/10$ of the modulation period.

2. A device as claimed in claim 1, wherein the high level corresponds to a rated emission value of the lamps.

3. A device as claimed in claim 1, wherein the low level corresponds to a substantially zero emission.

4. A device as claimed in claim 1, wherein for modulation of the lamp emission, the modulating means controls a corresponding envelope of the supply voltage of the lamps.

5. A device as claimed in claim 1, wherein it comprises means for heartbeat detection which is connected to the modulating means for modulation control depending on the detected heartbeat.

6. A device as claimed in claim 5, wherein the detection means operates passage between one level and the other on detection either of a systole or a diastole, at pleasure, in the heartbeat.

7. A device as claimed in claim 6, wherein, after a controlled passage, the reached level is maintained for a predetermined period of time.

8. A device as claimed in claim 7, wherein it comprises manual commands for keying in said predetermined period of time.

9. A device as claimed in claim 5, wherein the heartbeat-detecting means and the modulating means are connected with each other by a cordless connection.

10. A device as claimed in claim 9, wherein the cordless connection is a connection by radio.

11. A device as claimed in claim 9, wherein the cordless connection is an infrared-ray connection.

12. A device as claimed in claim 5, wherein it comprises means for controlling modulation with a predetermined advance relative to a heartbeat.

13. A device as claimed in claim 12, wherein the means for controlling modulation with an advance comprises means for measuring the average time between detected heartbeats, means for calculating the expected instant for the next heartbeat starting from said average time, means for controlling modulation with a predetermined advance relative to said expected instant for the next heartbeat.

14. A device as claimed in claim 1, wherein the infrared emission has a wavelength included between 0.76 and 1.5 micron.

15. A device as claimed in claim 1, wherein it comprises lamps for blue/ultraviolet emission, the emission of which is modulated in counter-phase with respect to the emission of the infrared lamps.

16. A device as claimed in claim 1, wherein it comprises means for application of a physical activity consisting of pedals on which a user pedals while being exposed to said lamps.

\* \* \* \* \*